(12) United States Patent
Sarma

(10) Patent No.: US 7,439,344 B2
(45) Date of Patent: Oct. 21, 2008

(54) SELECTIVE O-ACYLATION OF NUCLEOSIDES

(75) Inventor: Keshab Sarma, Sunnyvale, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 203 days.

(21) Appl. No.: 11/525,889

(22) Filed: Sep. 22, 2006

(65) Prior Publication Data

US 2007/0066815 A1     Mar. 22, 2007

Related U.S. Application Data

(60) Provisional application No. 60/719,776, filed on Sep. 22, 2005.

(51) Int. Cl.
- C07G 3/00      (2006.01)
- C07H 15/00     (2006.01)
- C07H 17/00     (2006.01)
- A01N 43/04     (2006.01)
- A61K 31/70     (2006.01)

(52) U.S. Cl. .................. 536/18.6; 536/18.5; 536/25.3

(58) Field of Classification Search .................. None
See application file for complete search history.

(56) References Cited

U.S. PATENT DOCUMENTS

2006/0040890 A1    2/2006   Martin et al.

OTHER PUBLICATIONS

Bobeck, M., et al. "Acetylenic nucleosides. 4. 1(β-D)-arabinofuranosyl-5-ethynyl-cyrosine. Improved synthesis and evaluation of biochemical and antiviral properties," *J. Med. Chem* (1987) vol. 30(11), pp. 2154-2157.

Breiner, R. G., et al. "Synthesis of new nucleosides phosphoraziridines as potential site directed Antineoplastic agents," *J. Med. Chem.* (1990) vol. 33(9), pp. 2596-2602.

Giorgi, T. et al. "Supramolecular Helices via Self-Assembly of 8-Oxoguanosines," *J. Am. Chem. Soc.* (2003) vol. 125(48), pp. 14741-14749.

Martinez, A.P., et al. The acetylation of 1-(β-D-arabinofuranosyl) cytosine[1], *J. Med. Chem.* (1966) vol. 9(2), p. 268.

Matsuda, A. "A Convenient Method for the Selective Acylation of Guanine Nucleosides," *Synthesis* (1986), pp. 385-386.

Ohno, M., et al. "Modulation of adenosine receptor affinity and intrinsic efficacy in adenine nucleosides substituted at the 2-position," *Bioorg Med. Chem* (2004) vol. 12, pp. 2995-3007.

Sekine, M. "Selective and rapid O-acylation of hydroxy groups of nucleosides by means of Phase transfer catalysis," *Nat. Prod. Res.* (1993) 1(4), pp. 251-256.

Zinni, M. A. et al. "Enzymatic Alcoholysis of 3',5'-di-O-acetyl-2'-deoxynucleosides," *J. Molecular Cat. B Enzymatic* (2004) vol. 29 pp. 129-132.

*Primary Examiner*—Patrick T Lewis
(74) *Attorney, Agent, or Firm*—Brian L. Buckwalter

(57) ABSTRACT

The present invention relates to a one-step process for the selective O-acylation of the hydroxy groups of a nucleoside under basic conditions utilizing DMAP and a carboxylic acid anhydride in aqueous heterogenous solvent mixture.

17 Claims, No Drawings

SELECTIVE O-ACYLATION OF NUCLEOSIDES

REFERENCE TO PRIOR APPLICATIONS

This application claims the benefit of priority to U.S. Ser. No. 60/719,776 filed Sep. 22, 2005 which is hereby incorporated by reference in its entirety.

FIELD OF THE INVENTION

The present invention relates to a one-step process for the selective O-acylation of the hydroxy groups of a nucleoside in heterogeneous aqueous solvent mixture under basic conditions utilizing DMAP and a carboxylic acid anhydride.

BACKGROUND

Nucleoside compounds are composed of a sugar moiety, typically ribose or 2-deoxyribose in naturally-occurring nucleosides, and a heterocyclic base which typically is adenine, guanidine, cytosine, thymine or uracil. Many nucleosides have basic amino substitution on the heterocyclic base and exhibit chemical reactivity characteristic of amino alcohols. The nitrogen atom of amino alcohols is frequently the most reactive and readily acylated functional group.

Nucleoside compounds and derivatives thereof have assumed an important role in the chemotherapy of viral and neoplastic diseases (see, e.g. P. L. Sarma et al., *Curr. Top. Med. Chem.* 2004 4:895-919; W. B. Parker et al., *Curr. Opin. Invest. Drugs* 2004 5(6):592-596). While nucleoside derivatives are frequently potent chemotherapeutic agents, their clinical use is often limited by suboptimal physical properties which result in poor pharmacokinetic profiles. Nucleoside prodrugs sometimes exhibit increased potency, bioavailability, stability which results in enhanced delivery of therapeutically effective amounts of the active moiety to the cellular target. Alkylation, acylation or other lipophilic modification of functional groups on the nucleoside often enhance passive diffusion through the intestinal wall (transcellular transport). Alternatively functional groups may be linked which are substrates for carrier-mediated transport systems resulting in an active transport of the prodrug. J.-L. Kraus et al., *Curr. Med. Chem.* 2003 10(18):1825-1846; P. Ettmayer et al., *J. Med. Chem.*, 2004 47(10):2393-2404; K. Beaumont et al., *Curr. Drug Metab.* 2003 4:461-485; H. Bundgaard, *Design of Prodrugs: Bioreversible derivatives for various functional groups and chemical entities in Design of Prodrugs*, H. Bundgaard (ed) Elsevier Science Publishers, Amsterdam 1985; G. M. Pauletti et al., *Adv. Drug Deliv. Rev.* 1997 27:235-256; and K. Beaumont et al., *Curr. Drug Metab.* 2003 4:461-485).

One strategy for prodrug design applicable to nucleosides is acylation of the hydroxyl substituents on the sugar moiety. Selective tri-acylation of the sugar residues of uridines has been reported (H. B. Lassan et al., *Nucleoside Nucleotides* 1998 17(9-11):1851-1856 and C.-T. Chen et al., *Org. Lett.* 2001 3(23):3729-3732.). Selective O-acylation of hydroxy groups of thymidine and uridine nucleosides under phase transfer conditions has been reported (M. Sekine, *Nat. Prod. Lett.* 1993 1(4):251-256). Nucleosides substituted with heterocyclic bases with an amino substituent are less likely to undergo such selective transformations. The preparation of 1-(2,3,5-tri-O-acetyl-β-D-arabinofuranosyl)cytosine hydrochloride (ara-C HCl) utilizes a two-step process comprising peracetylation and selective hydrolysis of the N-acetyl linkage with anhydrous ZnBr$_2$, MeOH and CHCl$_3$ (M. Bobeck et al., *J. Med. Chem.* 1987 30(11):2154-2157). A similar two-strategy for preparing tri-O-acyl derivatives of 4-amino-1-((2R,3R,4S,5R)-5-azido-3,4-dihydroxy-5-hydroxymethyl-tetrahydro-furan-2-yl)-1H-pyrimidin-2-one was reported by J. A. Martin et al., in U.S. Pat. No. 6,846,810 filed Nov. 19, 2003. Selective O-acylation of the sugar substitutents of cytosine-containing nucleosides under acidic conditions has been reported to result in O-acylation of cytidine, 2'-deoxycytidine and ara-C, R. G. Breiner et al., *J. Med. Chem.* 1990 33(9):2596-2602; A. P. Martinez et al., *J. Med. Chem.* 1966 9(2):268). While not wishing to be limited by a mechanistic hypothesis, these transformations were carried out under acidic conditions which protonate the amino substituent on the base and thereby suppress N-acylation. Selective O-acylation of guanosine and deoxyguanosine nucleosides with acetic anhydride in the presence of MeCN/TEA/DMAP (catalytic quantity) has been reported (A. Matsuda et al., *Synthesis* 1986 385-386). Selective O-acylation of cytidine under similar conditions has been reported (M. A. Zinni et al., *J. Mol. Cat. B* 2004 29:129-132). While these conditions result in some selective O-acylated product, the yields of O-acylated product are not acceptable.

SUMMARY OF THE INVENTION

The present invention provides a process for the selective O-acylation of a nucleoside of formula I under basic conditions in a heterogeneous aqueous solvent mixture wherein:

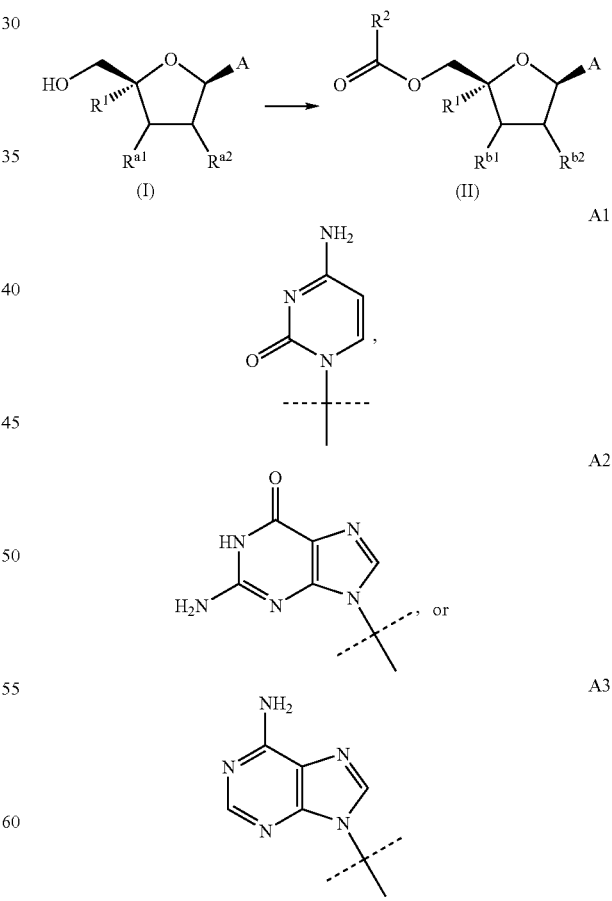

A is A1, A2 or A3
$R^1$ is hydrogen, azide, $C_{1-6}$ alkyl or $C_{1-3}$ acyl;
$R^{a1}$ and $R^{a2}$ are independently hydrogen or hydroxyl;

$R^{b1}$ and $R^{b2}$ are hydrogen or —$O_2CR^2$; and,
$R^2$ is $C_{1-10}$ alkyl or phenyl;
which process comprises the steps of:
(i) dissolving I and DMAP in an heterogenous aqueous solvent mixture and adding aqueous base to adjust the pH from 7 to 13;
(ii) optionally adding sufficient saturated aqueous NaCl to produce a biphasic reaction mixture;
(iii) adding an acylating agent and additional base sufficient to maintain the pH from 7 to 13;
(iv) monitoring the reaction and discontinuing addition of said acylating agent and said base when the conversion reaches a satisfactory level;
(v) optionally contacting the O-acyl nucleosides with a pharmaceutically acceptable acid to permit isolation of an acid additional salt of the O-acyl nucleoside.

DETAILED DESCRIPTION OF THE INVENTION

Acylated nucleosides are useful prodrugs which allow efficient delivery of therapeutically effective amounts biologically active nucleosides to patients. In addition, O-acylated nucleoside derivatives are frequently useful chemical intermediates for the preparation of nucleoside analogs. Selective acylation of natural nucleosides or derivatives thereof is often problematical due the plurality of reactive sites in many nucleosides. This is particularly true with nucleoside derivatives with a basic amine substituent on the heterocyclic base which frequently is the most reactive functional group in the molecule. The chemical reactivity of the substitutents sometimes limits the reagents which may be used for chemical transformations. Substitution of the ribose with azide has afforded several new pharmaceutically active compounds. Unfortunately the azide group may prove to be unstable in acidic media and the azide substituent is thermally labile and therefore an explosion hazard. Furthermore additional substitution on the sugar moiety can substantially alter the reactivity observed with natural nucleosides which lack said substitution. Conditions for selective acylation at low temperature under non-acidic conditions are therefore desirable. Large scale production of chemical compounds imposes further limitations on the reagents which can be utilized. Reactions which can be carried out in non-flammable solvents that can be easily recycled or discarded as waste are advantageous. Furthermore processes are desirable that limit the number of discrete chemical steps and unit operations both of which can add to production costs. Thus processes which do not require introduction of protecting groups are desirable. The present process has proven to be an effective and general route for the selective acylation of nucleosides.

In one embodiment of the present invention there is provided a process for O-acylation of nucleoside compounds comprising dissolving the nucleoside compound to be acylated in a heterogeneous aqueous organic solvent mixture and optionally adding sufficient brine to form a two phase mixture if required to produce two phases and adding DMAP to the biphasic mixture. The resulting solution is cooled to approximately 5° C. and sufficient base is added to adjust the pH to between about 7 and about 13 and an acylating agent is added. The reaction is monitored by a convenient technique and additional acylating agent may be added until the reaction reaches the desired endpoint. Additional base is added as required to maintain the pH in the desired range. During reaction workup, the product can optionally be contacted with a pharmaceutically acceptable acid to allow isolation of an acid addition salt of the O-acyl nucleoside. In the illustrative examples herein the acylating agent is the anhydride of a lower alkanoic acid; however one skilled in the art will appreciate that numerous alternative acylating agents are know and these can be used interchangeably in the present reaction conditions.

Aqueous solvents which are useful in the present process include aqueous THF, aqueous dioxane, aqueous acetonitrile, aqueous methyl tert-butyl ether and aqueous EtOAc.

In another embodiment of the present invention there is provided a process as described herein above for the selective O-acylation of ribose or arabinose derivative according to formula I wherein $R^{a1}$ and $R^{a2}$ are OH. One skilled in the art will appreciate that all embodiments also include deoxyribose and deoxyarabinose compounds (where $R^{1a}$ and/or $R^{a2}$ is hydrogen). It also should be clear that if $R^{1a}$ and/or $R^{2a}$ is/are hydrogen, then $R^{1b}$ and/or $R^{2b}$ respectively also is/are hydrogen.

In another embodiment of the present invention there is provided a process as described herein above for the selective O-acylation of a ribose or arabinose derivative according to formula I wherein $R^1$ is hydrogen or azide and $R^{a1}$ and $R^{a2}$ are OH.

In another embodiment of the present invention there is provided a process as described herein above for the selective O-acylation of a ribose or arabinose derivative according to formula I wherein $R^1$ is azide and $R^{a1}$ and $R^{a2}$ are OH.

In another embodiment of the present invention there is provided a process as described herein above for the selective O-acylation of a ribose or arabinose derivative according to formula I wherein $R^1$ is alkyl or acyl and $R^{a1}$ and $R^{a2}$ are OH.

In another embodiment of the present invention there is provided a process as described herein above for the selective acylation of a ribose or arabinose derivative according to formula I wherein $R^1$ is hydrogen or azide, $R^{a1}$ and $R^{a2}$ are OH and A is A1 (4'-azido-cytidine or 4'azido-araC), A2 (4'-azido-guanosine) or A3 (4'-azido-adenosine)

In another embodiment of the present invention there is provided a process as described herein above wherein the heterogeneous aqueous organic solvent mixture an aqueous ether. In yet another embodiment of the present invention there is provided a process as described herein above wherein the heterogeneous aqueous organic solvent mixture is aqueous THF.

In another embodiment of the present invention there is provided a process as described herein above wherein said pH range is from about 7.5 to about 12. In yet another embodiment of the present invention there is provided a process as described herein above wherein said pH range is from about 8 to about 10. In still yet another embodiment of the present invention there is provided a process as described herein above wherein said pH range is from 7 to 12.

In another embodiment of the present invention there is provided a process as described herein above wherein the base is aqueous alkali metal hydroxide, aqueous alkali metal bicarbonate or alkali metal carbonate.

In another embodiment of the present invention there is provided a process as described herein above wherein the base is aqueous potassium or sodium hydroxide.

In another embodiment of the present invention there is provided a process as described herein above wherein the acylating agent is a carboxylic acid chloride, a carboxylic acid anhydride or an acyl imidazole.

In another embodiment of the present invention there is provided a process as described herein above wherein the acylating agent is butyric anhydride, isobutyric anhydride, hexanoic anhydride, pentanoic anhydride or benzoic anhydride.

In another embodiment of the present invention there is provided a process as described herein above wherein the acylating agent is isobutyric anhydride.

In another embodiment of the present invention there is provided a process as described herein above wherein the nucleoside is 4'-azido-cytidine or 4'-azido-araC, the aqueous organic solvent is aqueous THF, the aqueous base is aqueous NaOH, the pH range is from about 8 to about 10 and the acylating agent is isobutyric anhydride.

In another embodiment of the present invention there is provided a process as described herein above wherein the nucleoside is 4'-azido-cytidine or 4'-azido-araC, the aqueous organic solvent is aqueous THF, the aqueous base is aqueous NaOH, the pH range is from about 8 to about 10 and the acylating agent is isobutyric anhydride which process further comprises the step of contacting the O-acylated nucleoside with pharmaceutically acceptable acid to produce an acid addition salt.

In another embodiment of the present invention there is provided a process as described herein above wherein the nucleoside is 4'-azido-cytidine or 4'-azido-araC, the aqueous organic solvent is aqueous THF, the aqueous base is aqueous NaOH, the pH range is from about 8 to about 10 and the acylating agent is isobutyric anhydride which process further comprises the step of contacting the O-acylated nucleoside with hydrochloric acid or methanesulfonic acid to produce a hydrochloride or methanesulfonic acid addition salt respectively. While this embodiment relates to the salt of a O-acyl 4'-azido-cytidine or 4'-azido-araC, the formation of a salt is a general process applicable to other O-acyl nucleosides.

In another embodiment of the present invention there is provided a method to acylate nucleoside derivatives wherein the base is uridine or optionally substituted thymine comprising dissolving the nucleoside compound to be acylated in a heterogeneous aqueous organic solvent mixture and optionally adding sufficient brine to form a two phase mixture if required to produce two phases and adding DMAP to the biphasic mixture. The resulting solution is cooled to approximately 5° C. and sufficient base is added to adjust the pH to between about 7 and about 13 and an acylating agent is added. The reaction is monitored by a convenient technique and additional acylating agent until the reaction reaches the desired endpoint. Additional base is added as required to maintain the pH in the desired range. During reaction workup, the product can optionally be contacted with a pharmaceutically acceptable acid to allow isolation of an acid addition salt of the O-acyl nucleoside. In the illustrative examples herein the acylating agent is the anhydride of a lower alkanoic acid; however one skilled in the art will appreciate that numerous alternative acylating agents (e.g., lower alkanoic acid chlorides) or methods to activate an alkanoic acid are known and these can be used interchangeably in the present reaction conditions. Acylation of uridine and thymidine derivatives is sometimes accompanied by formation of byproducts from O- and/or N-acylation of the uridine and thymidine which is not observed under the present conditions.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group or process step as provided in the Summary of the Invention or the most general embodiment of the invention.

"Optional" or "optionally" means that a subsequently described event or circumstance may but need not occur, and that the description includes instances where the event or circumstance occurs and instances in which it does not.

The term "acylating agent" as used herein refers to either an anhydride, acid halide, chlorocarbonylalkoxide (e.g., ethyl chloroformate). The term "anhydride" as used herein refers to compounds of the general structure RC(O)—O—C(O)R wherein R is as defined in claim 1. The term "acid halide" as used herein refers to compounds of the general structure RC(O)X wherein X is a halogen. The term "acyl imidazole" refers to a compound of general structure RC(O)X wherein X is N-imidazolyl. The term "activated derivative" of a compound as used herein refers to a transient reactive form of the original compound which renders the compound active in a desired chemical reaction, in which the original compound is only moderately reactive or non-reactive. Activation is achieved by formation of a derivative or a chemical grouping within the molecule with a higher free energy content than that of the original compound, which renders the activated form more reactive with another reagent. In the context of the present invention activation of the carboxy group is of particular importance and corresponding activating agents or groupings which activate the carboxy group are described in more detail below. Of particular interest for the present invention is carboxylic acid anhydrides and carboxylic acid chlorides.

The term "alkanoic acid" as used herein the term refers to a compound RC(O)OH wherein R is an alkyl group as defined herein. The term "lower alkanoic acid" refers to the group in which R is lower alkyl as defined herein.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. One or more of the carbon atoms may optionally be replaced by oxygen, sulfur, substituted or unsubstituted nitrogen atom(s). Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein.

The term azide as used herein refers to a $N_3$ ($N^-$=$N^+$=N—) group.

The phrase "heterogenous aqueous solvent mixture" as used here refers to a mixture of water and an organic co-solvent which produces a two-phase or heterogeneous mixture. This heterogeneous aqueous solvent mixture may result from a co-solvent with limited aqueous solubility or the ionic strength of the aqueous component can be adjusted (e.g., by the addition of brine) to limit the solubility of the co-solvent in the aqueous phase and thereby produce a heterogeneous system.

The term "carboxylic acid anhydride" as used herein refers to a compound with the general formula $(RCO)_2O$ wherein R is alkyl is defined herein or phenyl.

The term "alkali metal hydroxide" refers to a compound of formula MOH wherein M is lithium sodium, potassium or cesium, "alkali metal bicarbonate" refers to a group $MHCO_3$ wherein M is sodium or potassium and "alkali metal carbonate" refers to a group $M_2CO_3$ where M is sodium or potassium. One skilled in the art will appreciate that other bases can be used to maintain the pH with desired range and other bases are within the scope of the invention.

The term "nucleoside" as used herein refers a compound to a purine or pyrimidine base linked to the 1-position (anomeric carbon) of a carbohydrate. Ribose and arabinose, and deoxy or dideoxy derivatives thereof, are common carbohydrate components of nucleosides.

The terms "4'-azido-cytidine", 4'-azido-adenosine", "4'-azido-guanosine" and "4'-azido-araC refer to compounds (i)-(iv) respectively.

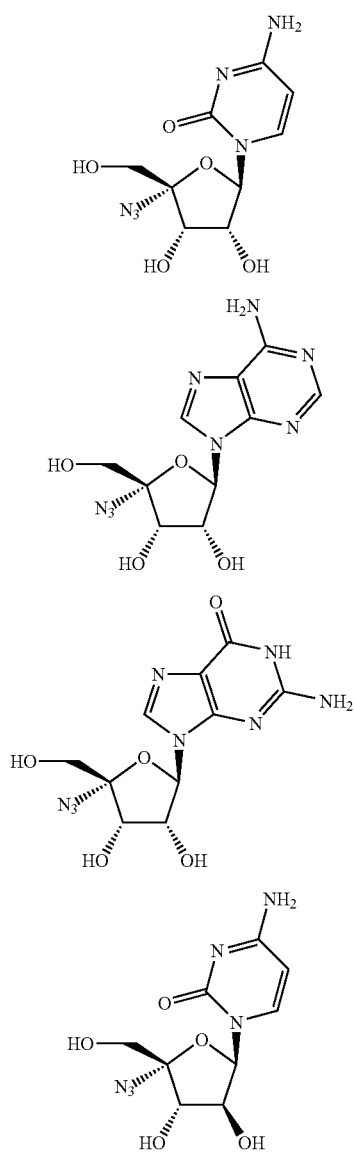

The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Abbreviations which may be found in this application include: acetyl (Ac), acetic acid (HOAc), 1-N-hydroxybenzotriazole (HOBt), atmospheres (Atm), high pressure liquid chromatography (HPLC), methyl (Me), tert-butoxycarbonyl (Boc), acetonitrile (MeCN), di-tert-butyl pyrocarbonate or boc anhydride ($BOC_2O$), 1-(3-dimethylaminopropyl)-3-ethylcarbodiimide hydrochloride (EDCI), benzyl (Bn), butyl (Bu), methanol (MeOH), benzyloxycarbonyl (cbz or Z), melting point (mp), carbonyl diimidazole (CDI), $MeSO_2$— (mesyl or Ms), 1,4-diazabicyclo[2.2.2]octane (DABCO), mass spectrum (ms), methyl t-butyl ether (MTBE), 1,5-diazabicyclo[4.3.0]non-5-ene (DBN), 1,8-diazabicyclo[5.4.0]undec-7-ene (DBU), N-methylmorpholine (NMM), N-methylpyrrolidone (NMP), 1,2-dichloroethane (DCE), N,N'-dicyclohexylcarbodiimide (DCC), pyridinium dichromate (PDC), dichloromethane (DCM), propyl (Pr), pounds per square inch (psi), diisopropylethylamine (DIPEA, Hunig's Base), pyridine (pyr), room temperature, rt or RT, N,N-dimethyl acetamide (DMA), tert-butyidimethylsilyl or t-$BuMe_2Si$, (TBDMS), 4-N,N-dimethylaminopyridine (DMAP), triethylamine ($Et_3N$ or TEA), N,N-dimethylformamide (DMF), dimethyl sulfoxide (DMSO), trifluoroacetic acid (TFA), thin layer chromatography (TLC), ethyl acetate (EtOAc), tetrahydrofuran (THF), diethyl ether ($Et_2O$), trimethylsilyl or $Me_3Si$ (TMS), ethyl (Et), p-toluenesulfonic acid monohydrate (TsOH or pTsOH), 4-Me—$C_6H_4SO_2$— or tosyl (Ts), iso-propyl (i-Pr), N-urethane-N-carboxyanhydride (UNCA), ethanol (EtOH). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

Examples of representative processes encompassed by the present invention and within the scope of the invention are provided in the following Examples. These examples are provided to enable those skilled in the art to more clearly understand and to practice the present invention. They should not be considered as limiting the scope of the invention, but merely as being illustrative and representative thereof.

EXAMPLE 1

Isobutyric acid (2R,3S,4S,5R)-5-(4-amino-2-oxo-2H-pyrimidin-1-yl)-2-azido-3,4-bis-isobutyryloxy-tetrahydro-furan-2-ylmethyl ester (2a)

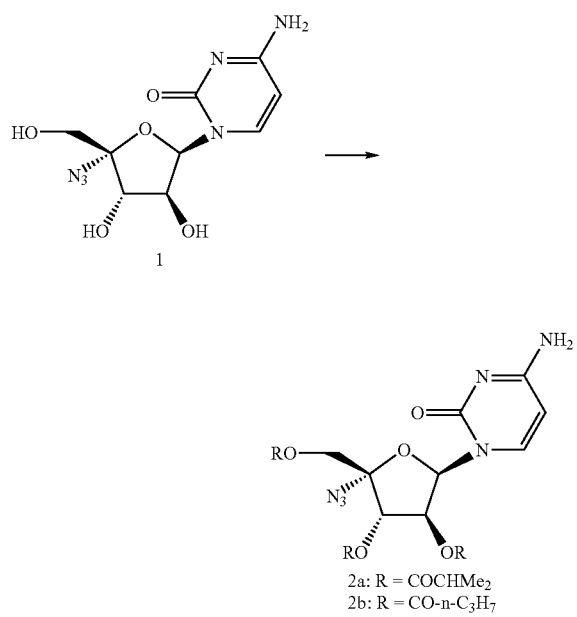

2a: R = COCHMe₂
2b: R = CO-n-C₃H₇

A solution of 4-amino-1-((2R,3S,4S,5R)-5-azido-3,4-dihydroxy-5-hydroxymethyl-tetrahydro-furan-2-yl)-1H-pyrimidin-2-one (1, 2.0 g, 7.04 mmol), THF (12 mL), water (8 mL) and DMAP (0.09 g 0.70 mmol) was treated with sufficient brine to produce a two-phase solution (approximately 2 mL). The resulting two-phase mixture was cooled to ca. 5° C. and isobutyric anhydride (3.56 g, 22.52 mmol) and 50% aqueous KOH were added simultaneously at a rate which maintained the pH of the reaction mixture at approximately 8.5. The progress of the reaction was followed chromatographically and starting material was consumed after addition of 3.2 equivalents of the anhydride. EtOAc (50 mL) was added and the organic phase was washed twice with dilute brine. The combined aqueous washes were twice extracted with EtOAc (15 mL). The two EtOAc washes were combined and was washed once with water. All the EtOAc extracts were combined, dried (Na₂SO₄) and concentrated in vacuo. The residue was dissolved in IPA (10 mL) and triturated with methanesulfonic acid (ca. 0.7 g). Heptane (10 mL) was added and the mixture solidified upon stirring at RT. A solution of heptane/IPA was added, the mixture was heated to 60° C. and allowed to cool slowly to RT. The resulting solid was filtered and washed with IPA/heptane and dried in a vacuum oven at 60° C. to afford 3.35 g (80.5% theory) of 2a: mp 167-169° C.).

Butyric acid (2R,3S,4S,5R)-5-(4-amino-2-oxo-2H-pyrimidin-1-yl)-2-azido-3,4-bis-butyryloxy-tetrahydro-furan-2-ylmethyl ester (2b, R=CO-n-C₃H₇; 1.45 g; 83.3% theory) was prepared in similar fashion except iso-butyric anhydride was replaced with butyric anhydride.

EXAMPLE 2

Isobutyric acid 5-(4-amino-2-oxo-2H-pyrimidin-1-yl)-2-azido-3,4-bis-isobutyryloxy-tetrahydro-furan-2-ylmethyl ester A slurry of 3 (12.0 kg) and DMAP (0.46 kg) in THF (48 L) and water (36 L) is treated with 50% aqueous KOH to adjust the pH to about 8.5. The resulting mixture is cooled to 10° C. and treated with isobutyric anhydride (21.6 kg) while maintaining the pH at about 8-11 (by simultaneous addition of 50% KOH) and the temperature at about 10-15° C. The reaction was monitored by HPLC and after the reaction was complete EtOAc (35 L) was added and the batch was filtered through CELITE®. The filtrate was separated into two phases and the aqueous phase was extracted twice with EtOAc (2×30 L). The combined EtOAc extracts were washed with dilute brine and EtOAc was distilled and replaced with IPA. The resulting solution was diluted with heptane which resulted in the precipitation of 4. The resulting slurry was aged at about 0° C. and the solid was isolated by filtration, washed with a heptane-IPA mixture and dried in a vacuum oven at about 50° C. to afford 17.01 kg (89% theory) of 4 which was 99.3% pure by hplc analysis.

EXAMPLE 3

Isobutyric acid 2-(6-amino-purin-9-yl)-4-isobutyryloxy-5-isobutyryloxymethyl-tetrahydro-furan-3-yl ester The title compound was prepared as described for example 1 from adenosine (5, 10 g; 37.42 mmol), DMAP (0.46 g, 3.74 mmol), THF (40 mL) and H$_2$O (30.0 mL). A total of 5.8 equivalents of isobutyric acid anhydride were required for complete conversion which afforded 17.8 g (100% theory of 6.

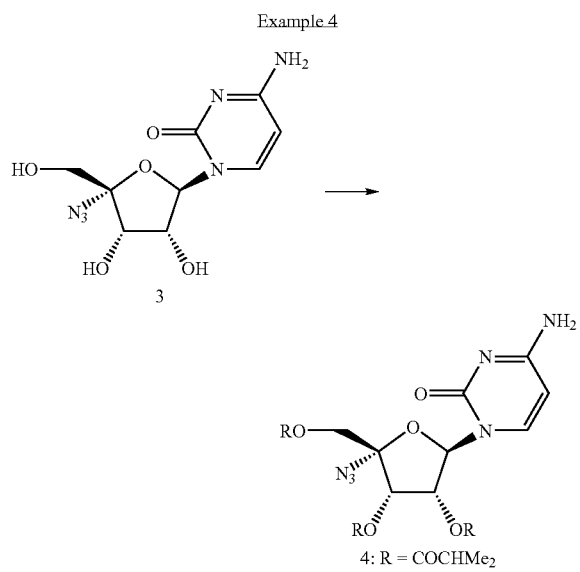

Acylation with an Acid Chloride

A solution of 4-amino-1-((2R,3S,4S,5R)-5-azido-3,4-dihydroxy-5-hydroxymethyl-tetrahydro-furan-2-yl)-1H-pyrimidin-2-one (3, 6.0 g, 18.01 mmol), THF (35 mL), brine (10 mL) and DMAP (0.2 g) was treated with sufficient brine to produce a two-phase solution (approximately 2 mL). The resulting two-phase mixture was cooled to ca. 5° C. and isobutyroyl chloride and 50% aqueous KOH were added simultaneously at a rate which maintained the pH of the reaction mixture at approximately 8.5. The reaction was monitored by HPLC and the addition was continued until all starting material was consumed. HPLC analysis indicated by tri- and tetra-acyl product was present. The pH of the reaction mixture was adjusted to ca. 1.5 with dilute H$_2$SO$_4$ and the reaction stirred overnight which resulted in hydrolysis of any tetra-acylated product. The product was extracted in EtOAc and the combined extracts were thoroughly washed with water adjusted to a pH of ca. 1.5. The resulting EtOAc solution was dried (MgSO$_4$), filtered and evaporated to afford 7.8 g of 4 which assayed to 85.3%.

Acylation with Carbonyl Diimidazole and Isobutyric Acid

To a slurry of 3 (1.0 g, 3.00 mmol), DMAP (37 mg), THF (1.0 mL) and water (4.0 mL) was added 50% NaOH until the pH was 7-8 and then adjusted to pH 9.5 with saturated NaHCO$_3$. Carbonyldiimidazole (1.3 g, 9.0 mmol) was added to a solution of isobutyric acid (0.8 g, 9.00 mmol) in THF (10 mL) and stirring continued until there was no further effervescence. The latter solution was added slowly to the slurry containing 3 at RT. The pH was maintained at ca. 9 by addition of base. HPLC analysis revealed a mixture of mono-, di- and triacylated product in which the latter two predominated. The reaction will proceed to completion if addition acyl imidazole is added until all material is converted to product.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

I claim:

1. A process for the selective O-acylation of a nucleoside I to afford a O-acyl nucleoside II under basic reaction conditions

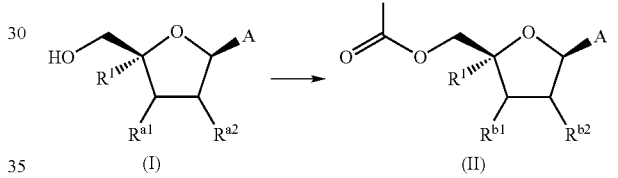

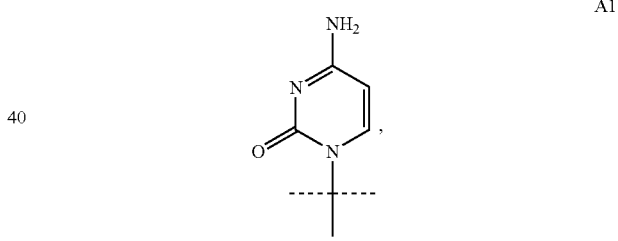

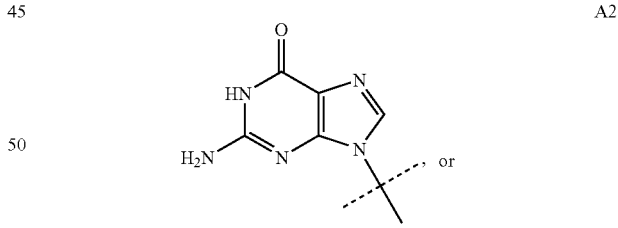

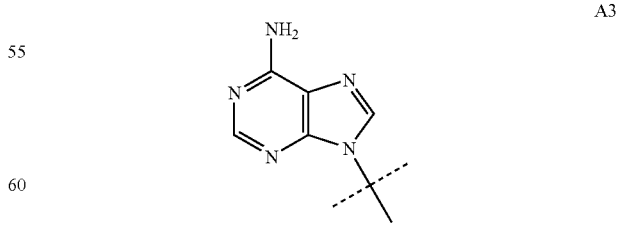

wherein:
  A is A1, A2 or A3
  R$^1$ is hydrogen, azide, C$_{1-6}$ alkyl or C$_{1-3}$ acyl;
  R$^{a1}$ and R$^{a2}$ are independently hydrogen or hydroxyl;

$R^{b1}$ and $R^{b2}$ are hydrogen or $-O_2CR^2$; and,
$R^2$ is $C_{1-10}$ alkyl or phenyl;
which process comprises the steps of:
(i) dissolving I and DMAP in an heterogeneous aqueous solvent mixture and adding aqueous base to adjust the pH from 7 to 13;
(ii) optionally adding sufficient saturated aqueous NaCl to produce a biphasic reaction mixture;
(iii) adding an acylating agent and additional base sufficient to maintain the pH from 7 to 13;
(iv) monitoring the reaction and discontinuing addition of said acylating agent and said base when the conversion reaches a satisfactory level;
(v) optionally contacting the O-acyl nucleoside with a pharmaceutically acceptable acid to permit isolation of an acid additional salt of the O-acyl nucleoside.

2. A process according to claim 1 wherein $R^{a1}$ and $R^{a2}$ are both OH and $R^{b1}$ and $R^{b2}$ are both $-O_2CR^2$.

3. A process according to claim 2 wherein $R^1$ is H or $N_3$.

4. A process according to claim 3 wherein $R^1$ is $N_3$.

5. A process according to claim 4 wherein said nucleoside of formula I is 4'-azidocytidine, 4'-azido-guanosine, 4'-azido-adenosine or 4'azido-ara-C.

6. A process according to claim 1 wherein said heterogeneous aqueous organic solvent is an aqueous ether.

7. A process according to claim 6 wherein said heterogeneous aqueous organic solvent is aqueous tetrahydrofuran.

8. A process according to claim 1 wherein said pH range is 7.5 to 12.

9. A process according to claim 8 wherein said pH range is 8 to 10.

10. A process according to claim 1 wherein said base is an alkali metal hydroxide an alkali bicarbonate or an alkali metal carbonate.

11. A process according to claim 9 wherein said base is KOH.

12. A process according to claim 1 wherein said acylating reagent is a carboxylic acid anhydride, acyl chloride, or an acylimidazole.

13. A process according to claim 12 wherein said acylating reagent is isobutyric, hexanoic, tripentanoic, butyric, or benzoic anhydride.

14. A process according to claim 13 wherein said acylating reagent is isobutyric anhydride.

15. A process according to claim 1 where said nucleoside of formula I is 4'-azidocytidine or 4'-azido-araC, said aqueous organic solvent is a biphasic aqueous tetrahydrofuran solvent, said base is NaOH, said pH range is about 8 to about 10 and said acylating reagent is isobutyric anhydride.

16. A process according to claim 14 wherein said process further comprising the step of contacting said O-acyl nucleoside with a pharmaceutically acceptable acid to produce an acid addition salt.

17. A process according to claim 15 wherein said pharmaceutically acceptable inorganic or organic acid is hydrochloric or methanesulphonic acid.

* * * * *